(12) United States Patent
Eilbert et al.

(10) Patent No.: US 7,369,642 B2
(45) Date of Patent: May 6, 2008

(54) X-RAY IMAGING TECHNIQUE

(75) Inventors: Richard F. Eilbert, Lincoln, MA (US); Alan R. Sieving, Waltham, MA (US)

(73) Assignee: L-3 Communications and Security Detection Systems Inc., Woburn, MA (US)

( * ) Notice: Subject to any disclaimer, the term of this patent is extended or adjusted under 35 U.S.C. 154(b) by 0 days.

(21) Appl. No.: 10/554,272

(22) PCT Filed: Apr. 20, 2004

(86) PCT No.: PCT/US2004/012110

§ 371 (c)(1),
(2), (4) Date: Dec. 8, 2006

(87) PCT Pub. No.: WO2004/095060

PCT Pub. Date: Nov. 4, 2004

(65) Prior Publication Data

US 2007/0147585 A1    Jun. 28, 2007

Related U.S. Application Data

(60) Provisional application No. 60/464,843, filed on Apr. 23, 2003.

(51) Int. Cl.
    *G01N 23/04*    (2006.01)
(52) U.S. Cl. .............................. 378/57; 378/62; 378/87
(58) Field of Classification Search ................... 378/4, 378/57, 62, 86, 87, 88, 90, 901; 250/208.1, 250/370.08, 370.09, 370.11
    See application file for complete search history.

(56) References Cited

U.S. PATENT DOCUMENTS

| 4,131,798 A |   | 12/1978 | Reddy et al. |
|---|---|---|---|
| 4,245,158 A |   | 1/1981 | Burstein et al. |
| 4,366,382 A |   | 12/1982 | Kotowski |
| 4,958,080 A |   | 9/1990 | Melcher |
| 5,040,199 A |   | 8/1991 | Stein |
| 5,044,002 A | * | 8/1991 | Stein ............................ 378/54 |
| 5,665,969 A |   | 9/1997 | Beusch |

(Continued)

OTHER PUBLICATIONS

Caria, Mario, Ed., "Radiation Imaging Detectors," Proceedings of the 3rd International Workshop on Radiation Imaging Detectors, Orosei, Sardinia, Italy, Sep. 23-27, 2001, Table of Contents.

(Continued)

*Primary Examiner*—Courtney Thomas
(74) *Attorney, Agent, or Firm*—Wolf Greenfield & Sacks

(57) ABSTRACT

A security system for detecting contraband such as explosives. The system has a source of radiation and a detector array. A detector array is made of many small detectors, each with a fast response time. The fast response time allows individual radiation photon interactions with each detector to be counted. By counting the number of interactions in an interval of time, the amount of radiation reaching the detector can be measured. The magnitude of the response from the detector to each radiation interaction allows measurement of the energy level of the photons interacting with the detector. Such a system provides significant flexibility in analyzing data collected from items under inspection. For example, objects such as contraband can be identified within the item under inspection by processing the data to accurately determine both the density and type of material.

49 Claims, 10 Drawing Sheets

U.S. PATENT DOCUMENTS 5,974,111 A * 10/1999 Krug et al. .................. 378/57
6,118,125 A    9/2000 Carlson et al.
6,248,990 B1   6/2001 Pyyhtiä et al.

OTHER PUBLICATIONS

Fischer, P., et al., "Single Photon Counting X-ray Imaging with Si and CdTe Single Chip Pixel Detectors and Multichip Pixel Modules," 3rd Int'l Workshop on Radiation Imaging Detectors, Orosei, Sardinia, Sep. 24-27, 2001.

Graeme, Jerald G., "Photodiode Amplifiers: Op Amp Solutions," McGraw-Hill, 1995, pp. v-31.

Melcher, C.L., et al., "A promising new scintillator: cerium-doped lutetium oxyorthosilicate," Nuclear Instruments and Methods in Physics Research, A314 (1992) pp. 212-214.

"Nuclear Isntruments and Methds in Physics Research Section A: Accelerators, Spectrometers, Detectors Table of Contents of and Associated Equipment," vol. 491, Issues 1-2, pp. 1-350 (Sep. 21, 2002), from Science Direct website http://www.sciencedirect.com/science, pp. 1-5, printed out Mar. 5, 2004.

Schirato, R.C., et al., "Development of monolithic $Cd_{1-x}Zn_xTe$ arrays with improved energy and spatial resolution," *SPIE*, vol. 2278 X-Ray and UV Detectors (1994), pp. 47-56.

Turchetta, R., et al., "High Spatial Resolution Silicon Read-Out System for Single Photon X-Ray Detection," IEEE Conference Record, Nuclear Science Symposium and Medical Imaging Conference, vol. 1, May 1994, pp. 435-439.

Van Eijk, C.W.E., "New inorganic scintillators—aspects of energy resolution," Nuclear Instruments and Methods in Physics Research, A471 (2001) pp. 244-248.

Search Report Dated Feb. 8, 2005.

* cited by examiner

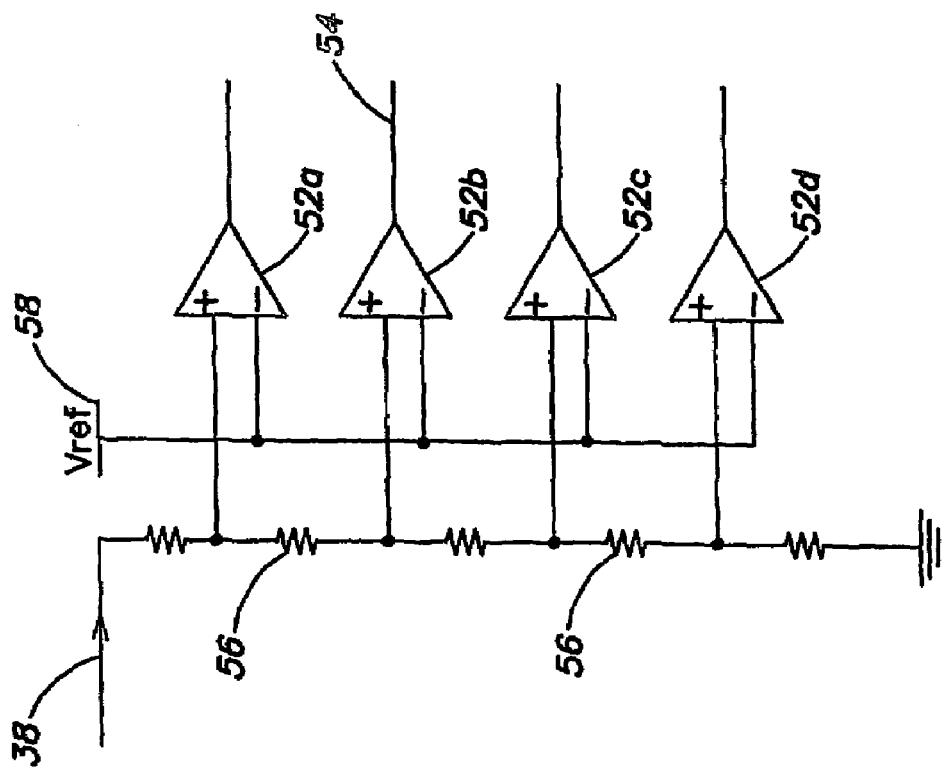
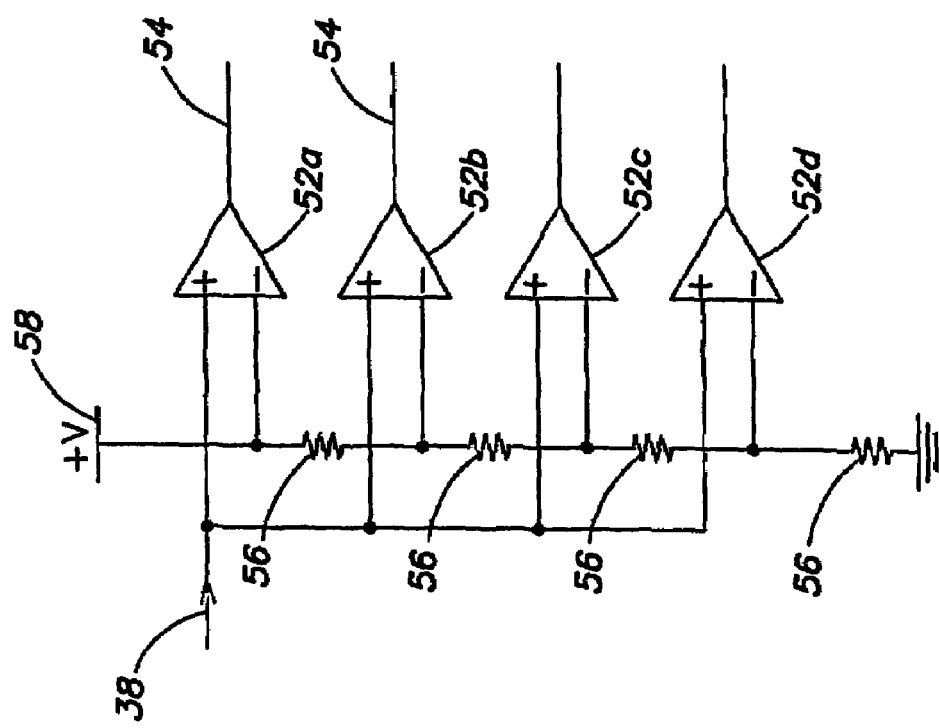
FIG. 5B
FIG. 5A

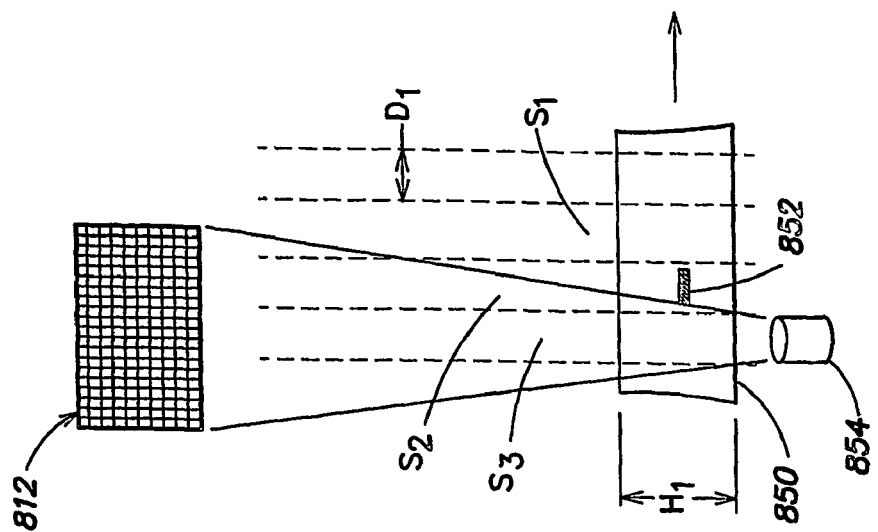
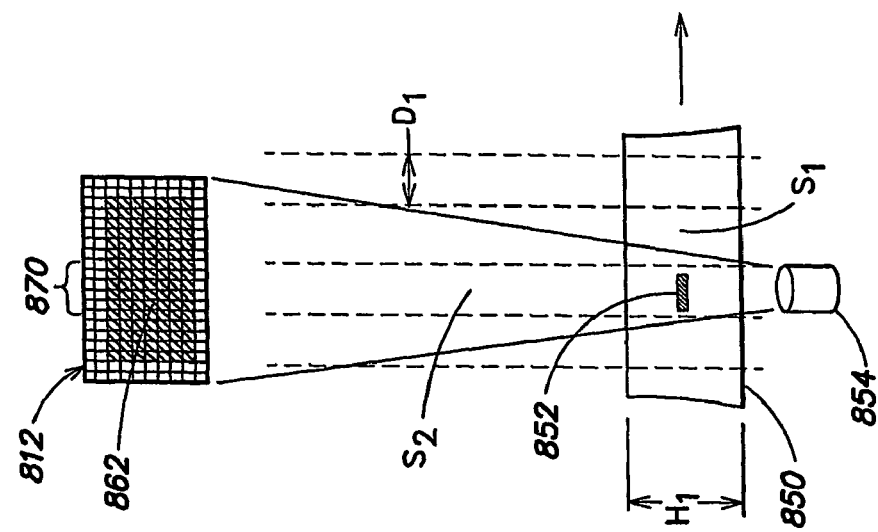
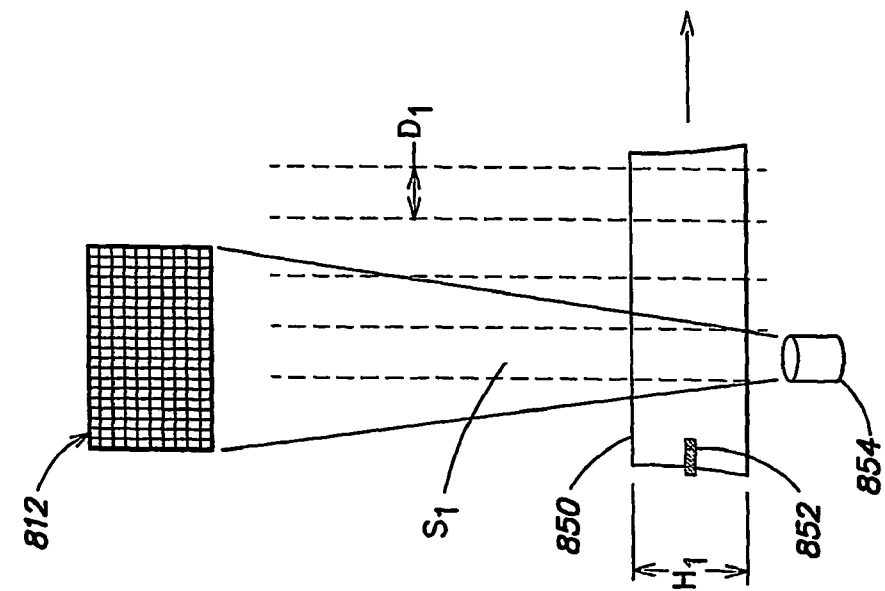
FIG. 8C
FIG. 8D
FIG. 8E

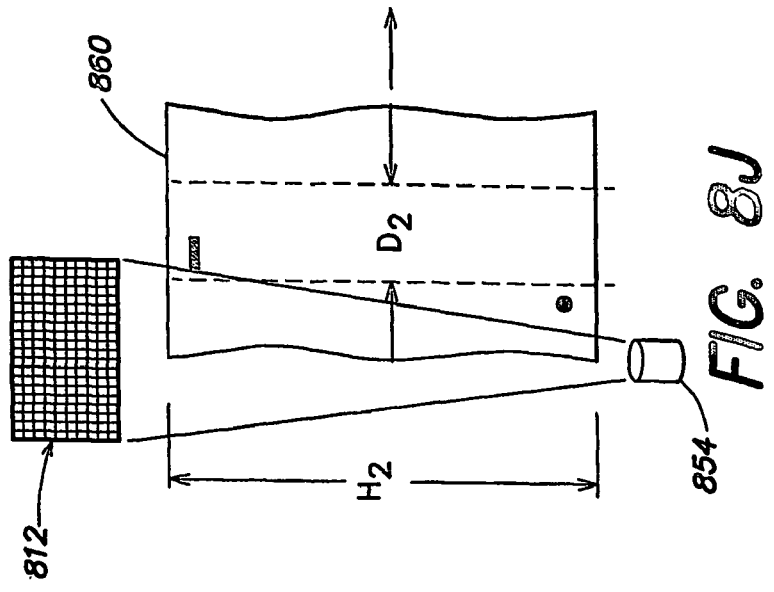
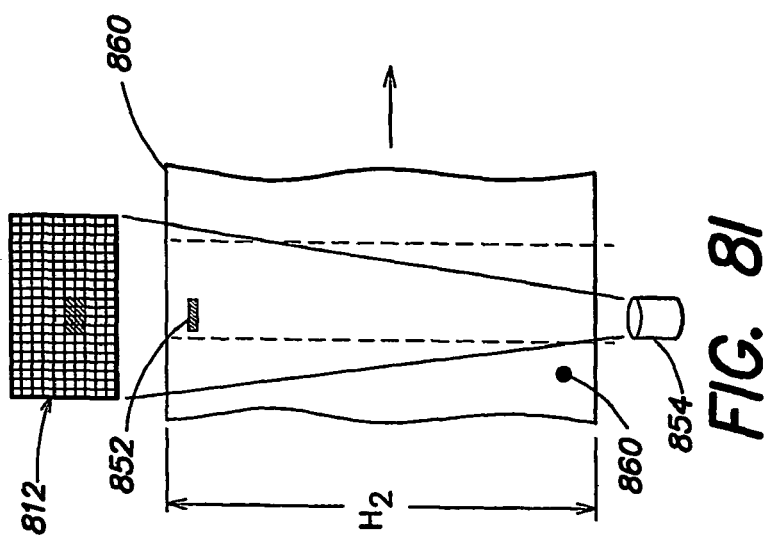
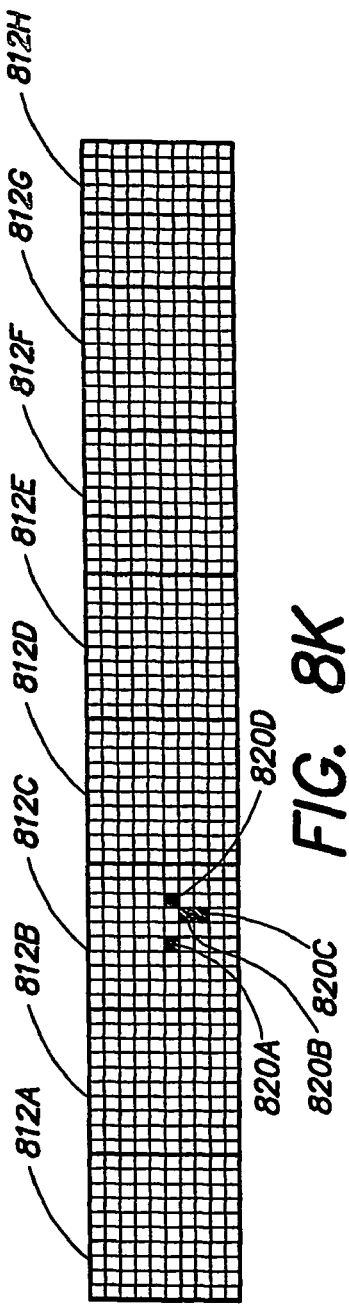

ic system's parts relative to the item under inspection, for example, without a conveyor.

X-RAY IMAGING TECHNIQUE

RELATED APPLICATIONS

This application claims priority under 35 U.S.C. § 119(e) to U.S. Provisional Application Ser. No. 60/464,843, entitled "X-RAY IMAGING TECHNIQUE," filed on Apr. 23, 2003, which is herein incorporated by reference in its entirety.

FIELD OF THE INVENTION

The present invention is directed toward an X-ray imaging technique, useful in threat detection systems, that includes detecting individual X-ray pulses that are transmitted through or scattered by an object under inspection.

BACKGROUND

Particularly at airports, it is often necessary or desirable to screen passenger baggage for potential threats or contraband items. X-ray baggage inspection systems typically operate by exposing an item of baggage to X-ray radiation and detecting the X-ray radiation that is transmitted through or scattered from the examined baggage. Some systems have used a single view source detector arrangement, while others have used dual view or multi-view arrangements. The single or dual view systems usually scan baggage as it moves on a conveyor, using a fan or scanning pencil source beam of X-ray radiation in a fixed geometry. Multi-view systems such as Computed Tomography (CT) systems usually perform a 360° scan of stationary baggage, and process data corresponding to absorption of the X-ray radiation from different scan angles to reconstruct a three-dimensional image of the baggage.

Conventional X-ray detection systems usually include an X-ray source and an X-ray detector located at an inspection region, and a conveyor which moves an object to be inspected through the inspection region. The X-ray source exposes an object under inspection to X-ray radiation at one or more energies. The X-ray detector detects X-ray radiation either transmitted through or scattered by the object under inspection to provide X-ray data. The X-ray detector may include a crystal scintillator formed of an array of cells which detect X-ray radiation and convert it to light. The array may be one- or two-dimensional, usually depending on whether the X-ray source produces a pencil beam or fan beam of X-ray radiation. Conventional dual energy X-ray detection systems require two separate X-ray detectors, one sensitive to higher energy X-rays, and another sensitive to lower energy X-rays.

Conventional X-ray systems sample the X-ray detector cells every 2-4 milliseconds (ms), and thus integrate the signal received from about 20,000 individual X-ray pulses during the sample period of approximately 4 ms. Because electronic noise is also accumulated during the sample period, the signal-to-noise ratio (SNR) obtained for highly attenuative objects may be too low for the system to accurately scan the objects for certain applications, such as airport security.

Cell to cell variability in an X-ray detectors is also common. This variability may be caused by flaws in the detector crystals, and differences in the decay time, light collection efficiency or temperature for the individual cells. Where these variations exist, two X-ray photons may deposit equivalent amounts of energy within the detector crystal, but the overall electrical response of the detector cell may be different. It may be desirable to be able to compensate for such variability so as to obtain better image resolution.

BRIEF DESCRIPTION OF THE DRAWINGS

In the drawings, in which like reference numerals indicate like elements;

FIG. 5a is a schematic diagram of one embodiment of a portion of a detector subsystem according to the invention;

FIG. 5b is a schematic diagram of another embodiment of a portion of a detector subsystem according to the invention;

FIGS. 8C, 8D, 8E, 8F, 8G, 8H, 8I, 8J, are sketches of a detector forming an image of an item moving relative to a radiation source;

FIG. 8K is a sketch of a linear array of detectors; and

DETAILED DESCRIPTION

The invention is directed to a novel X-ray detection system, useful in threat detection systems, based on a counting of individual X-ray pulses, instead of integrating a signal from many such pulses over relatively long time periods (e.g., 4 ms). The invention also includes methods for refining calibration of the detection system, particularly to compensate for cell-to-cell differences, to produce superior image and data quality.

Figure 1:
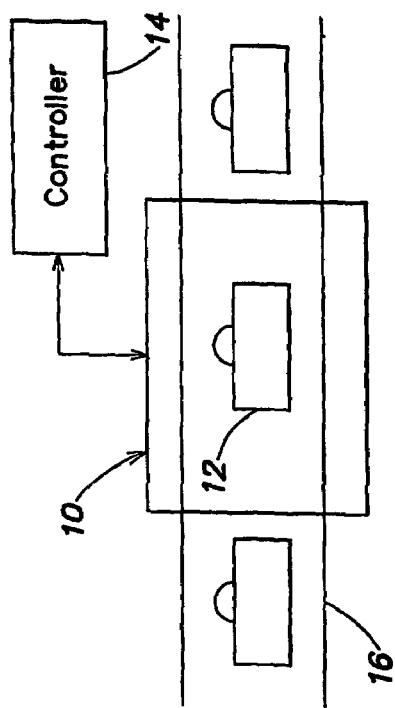
FIG. 1 is a schematic block diagram of a general baggage screening system.

Referring to FIG. 1, there is illustrated a schematic block diagram of a general baggage screening or inspection system comprising a detection system 10 that scans an item under inspection 12. The detection system is operatively coupled to a controller 14 that analyzes data about the item under inspection 12 collected by the detection system 10. The controller may include an operator interface and/or computing equipment constructed to detect, for example, suspicious region or objects within the item under inspection. Items may typically be moved through or passed the detection system 10 on a conveyor 16. However, it is to be appreciated that a detection system need not use a conveyor and may instead, for example, include means for moving the detection system 10 with respect to the item under inspection 12. For example, the detection system 10 may be located on a truck or other vehicle and may be moved past a stationary item under inspection 12 such as, for example, a vehicle to be inspected for contraband or threatening material. Therefore, while the following discussion will refer primarily to movable items under inspection being transported relative to the detection system 10 using a conveyor 16, it is to be appreciated that the invention is not so limited and may be applied to non-conveyorized systems.

The detection system 10 may usually comprise an X-ray source constructed to emit X-ray radiation and a detector that is constructed to detect X-ray radiation scattered by or transmitted through the item under inspection. The detector is usually adapted to detect X-ray interactions between X-ray pulses generated by the X-ray source and a detector material, as will be discussed in more detail below. However, it is to be appreciated that the detection system 10 is not limited to an X-ray radiation source and may instead of or in addition to an X-ray source, comprise a neutron or gamma ray source and a suitable detector. For clarity, the following discussion will refer primarily to X-ray sources and detectors, however it is to be understood that the invention applies also to other sources of radiation and corresponding detectors.

An example of a usual time period separating individual X-ray interactions, produced by X-ray radiation from an X-ray source impinging on a detector, at a given detector for cabinet or cargo x-ray systems, is approximately 200 nanoseconds (ns). Such x-rays may be produced from a conventional X-ray source, such as an X-ray tube. Other types of X-ray sources that may be used include Linac with generated X-rays, or a radioactive gamma source. In conventional baggage screening or threat detection systems, rather than attempt to detect such individual X-ray interactions every 200 ns, the detector includes circuitry that may integrate a signal over approximately 4 ms, corresponding to approximately 20,000 X-ray photon interactions with the scintillating detector crystal. Currently used crystal scintillators, for example Cesium Iodide (Cs) and Cadmium Tungstate ($CdWO_4$), have decay times in a range of approximately 1,000 to 20,000 ns. Thus, it is difficult to distinguish individual electronic pulses arising from an X-ray interaction with these scintillators because many such pulses overlap during the decay time period of the scintillator. This is known as pulse pile-up. Hence conventional systems integrate the signal over many X-ray interactions to obtain an average signal. Applicants herein have recognized that by using newer, high efficiency crystal scintillators, for example, lutetium oxysulfide, lutetium phosphorosulphide, lanthanum chloride or lanthanum bromide, which have rise and decay times in a range of approximately 25-40 ns, it is possible to detect accurately individual X-ray photon-crystal interactions.

Detecting individual X-ray photons is known in the field of X-ray spectroscopy and medical applications of radiation imaging. For example, an X-ray detector designed to operate as an imaging spectrometer that measures energy of individual X-ray photons detected by each pixel of the X-ray detector, is described in U.S. Pat. No. 5,665,969 (the '969 patent). The '969 patent describes a method of weighting, then summing the interactions of x-ray photons with the detecting crystal at different energy levels. For each detector pixel, only one value (which is a summed value) is passed on to contribute to the final image. By contrast, according to some dual or multi energy embodiments of the invention, for each pixel, a minimum of two detector values, one each for at least two different energy levels, are obtained (e.g., a high-energy pixel value and a low-energy pixel value resulting from detecting a transmitted high energy signal and a low energy signal). These at least two detector values are not weighted and summed together. Rather, the high-energy pixel value and the low-energy pixel value are used in a mathematical formula to estimate the atomic number of the material under inspection, or other quantities of interest for imaging. In other, single energy, embodiments of the invention, only one detector value may be obtained for each pixel, however, in these embodiments, the single detector value is still not a summed value.

Another example of a radiation imaging device that detects and counts the number of incident radiation hits (X-ray photons) at the detector is described in U.S. Pat. No. 6,248,990. The '990 patent describes a photon counting mechanism that is dependent upon the a silicon coupling mechanism, where an electrical interconnection between a counting substrate and an imaging substrate is made via bump bonds (such as Indium bonds). By contrast, the present invention is not dependent upon this interconnection mechanism.

In general there are at least three broad categories of detectors that may be used in X-ray or other radiation type scanning systems. A first includes a scintillator material that converts received X-ray radiation into light that may then be detected by a light-sensitive detector, such as, for example, a photodiode or photoresistor. A second type of detector includes a semiconductor material, such as, for example, Cadmium-zinc-telluride (CdZnTe), that produces an electronic pulse in response to received X-ray radiation. A third type of detector includes an ionization chamber that comprises a chamber having a plurality of wires disposed therein and is filled with an ionized gas. When X-ray interactions occur within the chamber, a current or voltage is induced on one or more of the detector wires that can be used to derive information about the occurring X-ray events. The invention is directed to using any one of class detector subsystems in a threat detection or baggage screening system wherein individual X-ray interactions are monitored. The following discussion will focus primarily on detector subsystems that include scintillators. However, it is to be appreciated that the invention is not so limited to scintillator type detectors, and the principles of monitoring individual X-ray (or other radiation type) events may be applied to detector subsystems that comprise ionization chambers, semiconductor materials, or other detector types used by those of skill in the art.

Figure 2:
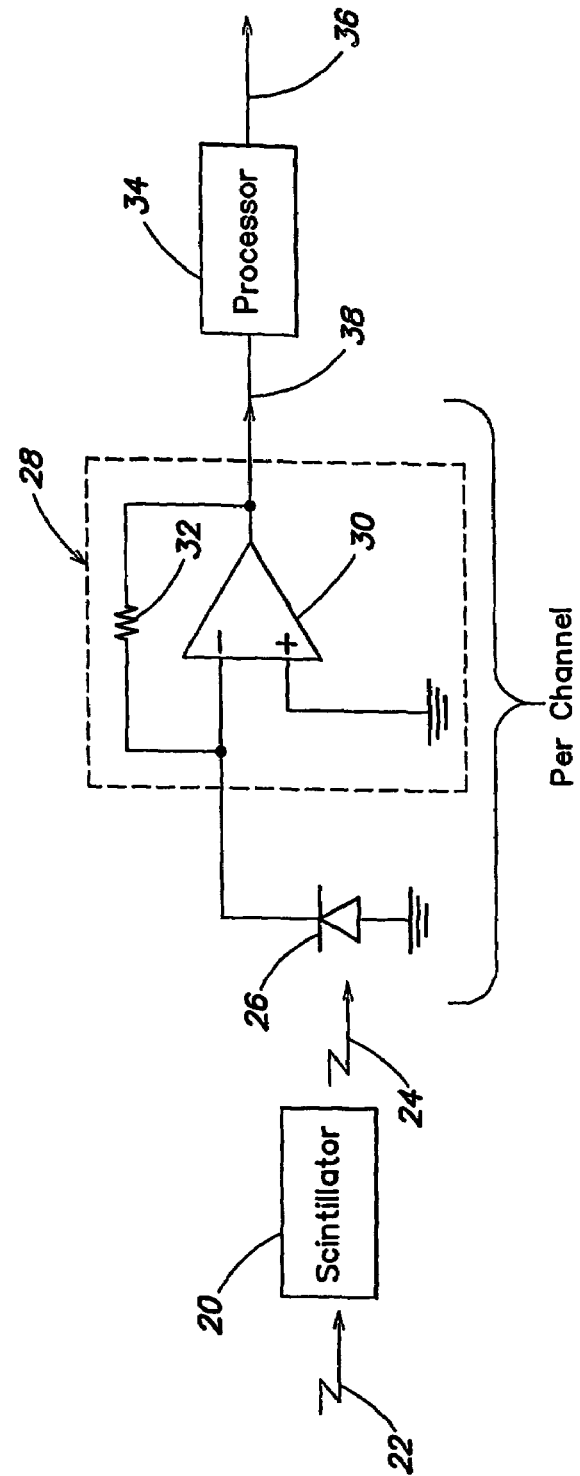
FIG. 2 is a schematic diagram of one embodiment of a portion of a detector subsystem according to the invention.

Referring to FIG. 2, there is illustrated a schematic diagram of one embodiment of a portion of a detector subsystem for one cell of a detector array according to aspects of the invention. The X-ray detector sub-system may include a crystal scintillator 20 that may detect X-ray photons 22 that are either transmitted through or scattered by an object under inspection (not shown, see FIG. 1). The scintillator 20 may be, for example, any of Lutetium Oxysulfide (LSO), Cesium iodide (CsI(Tl)), bismuth germinate (BGO), or another crystal structure or other material that converts X-ray photons to visible light photons. The scintillator 20 converts the X-ray photons 22 to light 24 which is detected by a photodetector 26. It is to be appreciated that although the photodetector 26 is illustrated as being a photodiode, the detector sub-system is not so limited, and the photodetector may be, for example, any of a photoresistor, an ionization chamber, a phototransistor, a charge-coupled device (CCD) or another type of photodetector known to those of skill in the art. The light is converted by the photodetector 26 into an electrical signal that may be amplified by an amplifier block 28. In the illustrated example, the amplifier block includes an operational amplifier 30 and a resistor 32, connected in a negative feedback loop, that at least in part controls a gain of the amplifier. However, it is to be appreciated that the amplifier block 28 may include additional components, such as, for example, additional resistors and/or one or more capacitors, and may also be implemented using components other than an operational amplifier, as known to those of skill in the art. The amplified signal may then be processed by processing electronics 34 to provide an output signal on line 36 that may be used to provide X-ray data.

The components illustrated in FIG. 2 convert an X-ray interaction at one cell in a detector subsystem array into an electrical signal, and ultimately into useful data, such as, for example, an image of an item under inspection or an effective atomic number of material within the item under inspection. It is to be appreciated that an entire detector subsystem may comprise many hundreds or even thousands of detector cells and the corresponding components illustrated in FIG. 2, except for processing electronics 34 which may likely be shared among cells, which may be provided for each cell in the detector array. It is further to be appreciated that the scintillator 20 and photodetector 26 may be replaced by a semiconductor material, for example, direct CdTe or CdZnTe, that may generate an electrical signal in response to received X-ray photons 22, which electrical signal may be directly applied to the amplifier block 28.

According to one example of a conventional system, a photodiode detector coupled to a CsI(Tl) scintillator (CsI(Tl) detector) in a cabinet x-ray system may integrate a signal over approximately 4 ms, corresponding to approximately 20,000 X-ray photon interactions with the scintillating detector crystal, to produce an integrated signal of 2,000 analog-to-digital conversion (A/D) counts in amplitude. Therefore, on average, each X-ray photon contributes approximately 0.1 A/D counts. In such a system, one A/D count may correspond to, for example, one millivolt (mV) of signal amplitude. However, it is to be appreciated that different systems may be calibrated differently and may have different sensitivities, and thus 1 A/D count may correspond to more or less than 1 mV. However, electronic noise accumulated over the sample period may also correspond to approximately 1 A/D count. Thus, it may be impossible to detect individual interactions of X-ray photons with the scintillating crystal (detector) because they are lost within the noise floor.

In contrast, by using individual, fast-response detector crystals for X-ray photon interactions over a time period of, for example, approximately 40 ns, the peak signal will be larger by a factor of 5, assuming that the scintillator used has the same light output efficiency as CsI This is because the same amount of light emission is concentrated in 0.8 ms (20,000×40 ns), which is only one fifth of the 4 ms sampling time described above. Accordingly, the output signal from the scintillator for each X-ray photon is approximately 0.5 A/D counts during the 40 ns time period. Electronic noise accumulated during the 40 ns time period would be ideally reduced (compared with the noise accumulated over a 4 ms time period) by the square root of $10^5$ (since 4 ms is equal to $10^5 \times 40$ ns), and thus would be approximately 0.003 A/D counts. Thus, the signal-to-noise ratio would be greatly improved and would be sufficiently high to allow individual X-rays to be detected accurately. This improved signal-to-noise ratio may also enable the system to scan highly attenuating objects that are difficult to scan using conventional systems.

Referring again to FIG. 2, the scintillator 20 may include a plurality of cells, each cell corresponding to a detector channel, such that the scintillator may detect X-rays over a desired area, such as a linear diode array or a 2-dimensional detector array. Each detector channel (cell) corresponds to a small section of an object being examined. For example, a detector array may include an array of 2000 cells, each observing a 2 mm section of the object under inspection. Processor 34 configured, for example, with suitable software, may be used to build-up an image of the item under inspection from the output signals provided by the detector array. Machine intelligence (for example, software or photo-edge-detectors, or other types of machine intelligence known to those of skill in the art) may be used to understand the "beginning" and "ending" of an individual object or group of objects (e.g., a suitcase).

As mentioned above, conventional dual energy X-ray detection systems employ two different detectors, one sensitive to higher energy X-rays, and another sensitive to lower energy X-rays. By contrast, by analyzing the individual X-ray interaction events, the invention enables dual energy detection using a single X-ray detector that detects both high energy and low energy X-rays. For example, in a system using an X-ray source with a peak energy of 150 kilovolts (such a source normally generates X-ray photons at a spectrum of energy levels), energy deposition from each x-ray interacting with the scintillator is nearly complete. The amplitude of a light signal generated by the scintillator for each X-ray photon interaction is proportional to the energy of the X-ray photon. Accordingly, higher-energy X-ray photons will release more visible light photons in the scintillator, and the photodetector will thus produce a stronger signal in response to a higher-energy X-ray. Similarly, lower-energy X-ray photons will produce a weaker signal in the photodetector. The individual signals provided by the photodetector can be analyzed to accomplish dual energy detection.

Figure 3:
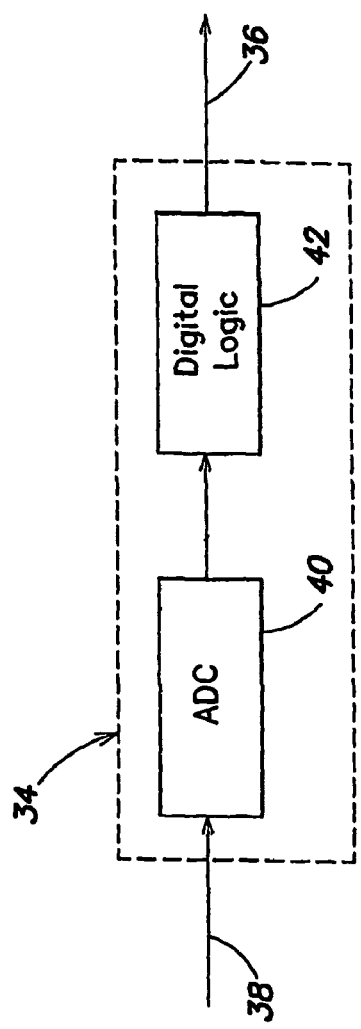
FIG. 3 is a schematic block diagram of an example of a processing block according to one embodiment of the invention.

Referring to FIG. 3, there is illustrated an example of a processing block 34 according to one embodiment of the invention. In this example, which measures the output detector signal pulse height, a signal from the photodetector may be received on line 38 by an analog-to-digital converter (ADC) 40, which in turn converts the signal to a digital value. The ADC 40 may be, for example, a 6-bit or 8-bit ADC, or a higher resolution ADC, if desired. A digital logic device 42 may receive the digital value from the ADC and provide X-ray data based on the digital value. The digital value is representative of the amplitude of the signal on line 38 that is received, via the amplifier block, from the photodetector, and which is in turn representative of the energy deposited by the X-ray photon. Thus, the size of the digital value is indicative of the energy deposited by the X-ray photon. Therefore, by digitizing the signal received from the detector for each X-ray interaction, dual-energy, or multi-energy, X-ray data may be obtained from a single X-ray detector.

Figure 4:
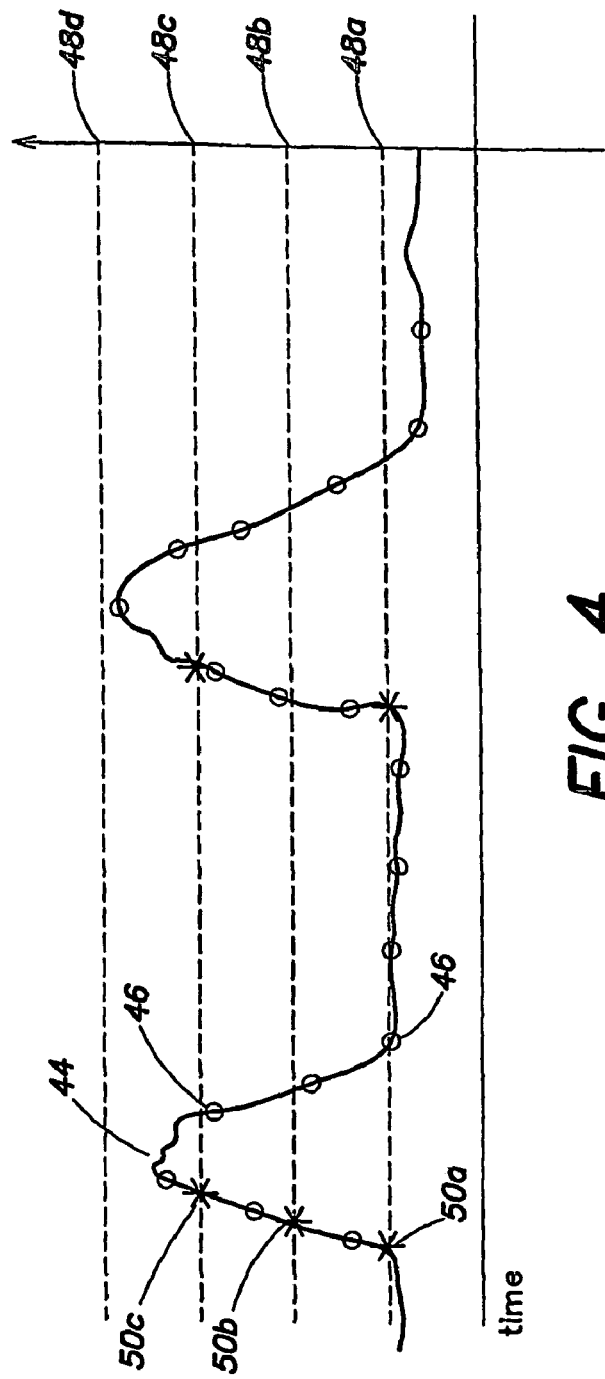
FIG. 4 is a graph of an example of a pulse signal that may be generated by the detector of one embodiment of the invention.

For example, referring to FIG. 4, the signal on line 38 (output from a detector) may include one or more pulses 44 generated by an X-ray interactions with the scintillator. The signal may be sampled, for example, at regular time intervals, at sample points 46, each of which may be converted to a digital value, representative of the amplitude of the signal at that sample point, by the ADC (FIG. 3, 40). However, such a sampling method, while it may provide an accurate reconstruction of the pulses 44, may produce a large amount of data which may be difficult to process and transfer to, for example, processing electronics at controller

14 (see FIG. 1). Such a sampling method may nonetheless be commercially useful as data transfer rates and computer processor speeds increase with technological advances.

An alternative to sampling the detector signal on line 38 at regular intervals, in order to, for example, reduce the data and/or sampling rate, the detector signal may be monitored to determine when the amplitude of the detector signal exceeds certain predetermined levels. For example, referring to FIG. 4, a plurality of predetermined levels 48a-d may be selected and provided by processor 34, and events 50a-c of the amplitude of pulse 44 exceeding the predetermined levels may be recorded or used to trigger, for example, a comparator, to produce a signal, as discussed in more detail below. It is to be appreciated that although four levels 48a-d are illustrated in FIG. 4, the invention is not so limited and may be adapted to use any number of levels, as desired.

According to one embodiment, illustrated in FIGS. 5a and 5b, one or more comparators 52 may be used to count electronic pulses from individual X-ray interactions that have an energy above certain predetermined set thresholds, as illustrated, for example, in FIG. 4. This embodiment provides for a type of X-ray detection apparatus with very low noise characteristic. The amplified signal on line 38 from the amplifier block (28, FIG. 2) may be provided at the inputs of one or more comparators 52. Each comparator 52 may output a logic 1 if the amplitude of the input signal is greater than a predetermined threshold, and may output a logic 0 on line 54 if the amplitude of the input signal is below the predetermined threshold. In one example, with a single comparator, electronic pulses from high energy X-ray events may exceed a predetermined threshold whereas random noise and low energy X-ray events may not. Therefore, with a single comparator, the number of X-ray events of interest may be counted. It is to be appreciated that a relatively short sample time may be needed for the comparator because the peak signal for a single X-ray photon interaction may not be distinguishable from the background noise unless the sample time is less than the arrival rate of X-ray photons.

According to another example, two comparators may be provided and thus a HI level and a LO level threshold may be set. By counting the number of HI and LO pulses, i.e., X-ray photons that respectively generate signals with amplitudes that exceed the predetermined HI and LO thresholds, dual energy X-ray data may be obtained using a single X-ray detector. Using one or more comparators to provide X-ray data may be advantageous because it may be a cheaper solution than using an ADC, and cheaper than providing two detectors and respective processing electronics.

Referring to FIG. 5a, the X-ray detector subsystem may be implemented using four comparators 52a-d, each configured to output a signal on line 54 that corresponds to a logic 1 when the amplified signal on line 38 applied to a respective positive input exceeds a certain predetermined threshold, for example, corresponding to the levels 48a-d illustrated in FIG. 4. The predetermined threshold may be set using, for example, a voltage divider that includes a plurality of resistors 56 connected between a voltage supply terminal 58 and the respective negative inputs of each of the comparators 52a-d. It is to be appreciated that FIG. 5b illustrates one example of an implementation of this embodiment, and numerous alterations or modifications may be apparent to those of skill in the art.

One such alternative is illustrated in FIG. 5b. In this example, the negative input terminals of the comparators 52a-d are connected to a reference voltage terminal 58, and the amplified signal on line 38 is supplied, via a voltage divider including a plurality of resistors 56, to the positive input terminals. Thus, the predetermined thresholds for each of the comparators 52a-d is the same, and the amplified signal is scaled by the resistors 56. This is an alternative to the example illustrated in FIG. 5a, where the amplified signal is applied, having a same amplitude, to the positive terminals of each of the comparators 52a-d and the predetermined threshold for each comparator is set by scaling the reference potential using the resistors 56.

It is to be appreciated that many other variations of these circuits that accomplish substantially the same result may be apparent to those of skill in the art. For example, the X-ray detector subsystem may be implemented using any number of comparators, not necessarily four as illustrated. Furthermore, additional components may be added to the circuit, such as, for example, blocking capacitors and/or additional resistors. Further, the output signals on lines 54 from each of the comparators 52a-d may be processed by digital logic to obtain X-ray data about an object under inspection.

Figure 6:
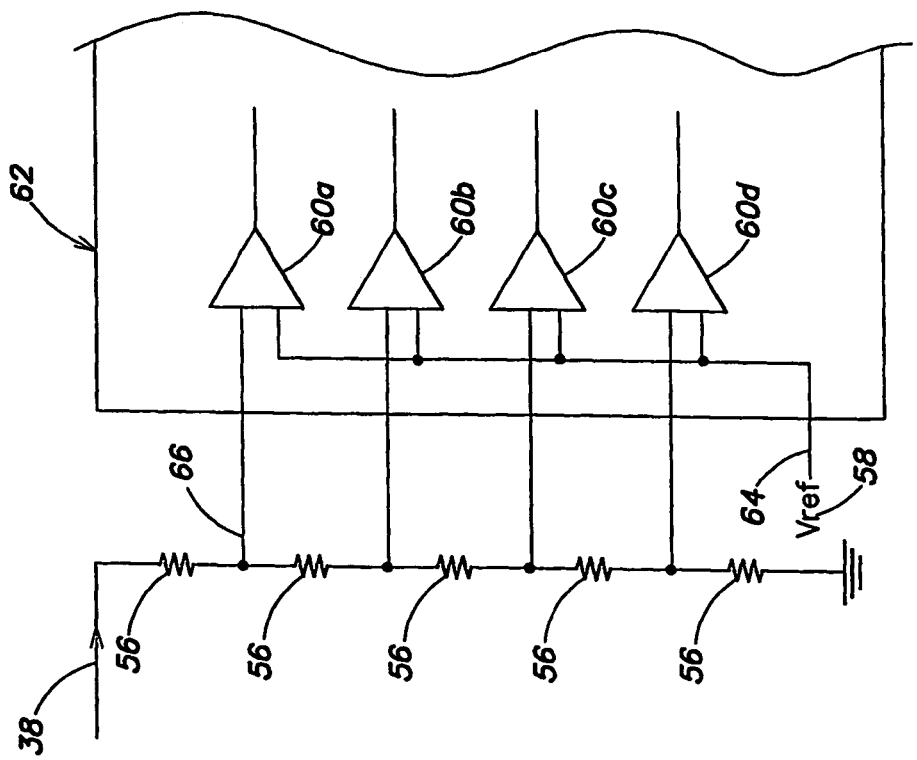
FIG. 6 is a schematic diagram of another embodiment of a portion of a detector subsystem according to the invention.

Referring to FIG. 6, there is illustrated yet another embodiment of a portion of an X-ray detector subsystem according to the invention. In this example, comparators 60a-d are formed as part of an integrated digital logic circuit 62, rather than being provided as discrete elements as illustrated in FIGS. 5a and 5b. The positive (and/or negative inputs) of the comparators 60 may be realized as pins 66 of the digital logic device 62, and the amplified signal on line 38 is provided to the pins 66 via a voltage divider including a plurality of resistors 56 (as discussed with reference to FIG. 5b). An additional pin 64 may be connected to an external reference voltage 58, and internally, may be connected to the negative input terminals of the comparators 60. Thus, the circuit illustrated in FIG. 6 operates equivalently to that illustrated in FIG. 5b, with the difference being that the comparators are implemented as part of the digital logic circuitry that processes the signals to provide the X-ray data.

Figure 7:
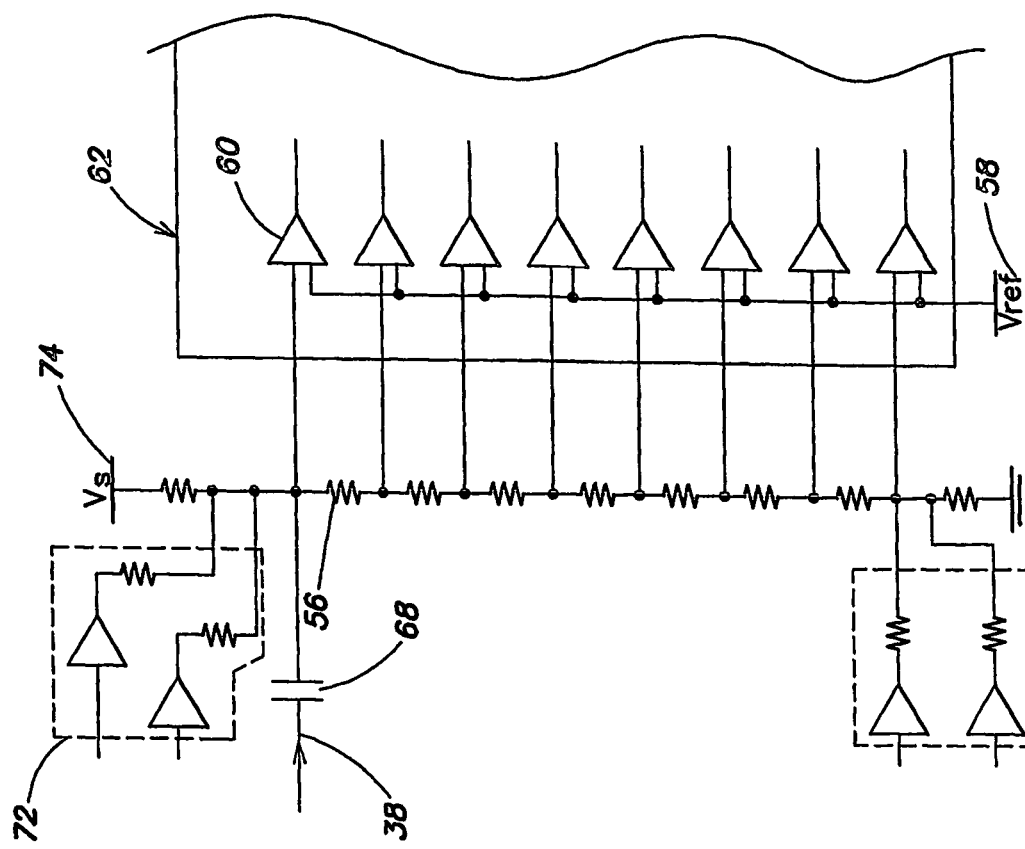
FIG. 7 is a schematic diagram of yet another embodiment of a portion of a detector subsystem according to the invention.

Furthermore, additional components may be included in the circuit, as is illustrated in FIG. 7. For example, a blocking capacitor 68 may be connected to the line 38 upon which the amplified signal is provided to the voltage divider. The blocking capacitor 68 may operate to block any unwanted DC components of signal on line 38, such that only incremental changes in the signal are passed through the blocking capacitor 68, which may be then measured by the comparators 60. In addition, component blocks 70 and 72 may be provided to adjust the upper and lower threshold values presented to the inputs of the comparators 60. Blocks 70 and 72 are illustrative of circuits which may provide an offset to the signal on line 38. This offset may be adjusted to vary the response of the comparators 60 in order to calibrate the system, or to tune the response of the system, as discussed in more detail below. It is to be appreciated that blocks 70 and 72 are illustrative only, and may be replaced by other configurations with more or fewer components, to provide an offset. A supply voltage 74 may also be applied to the voltage divider chain of resistor 56 in order to further set the desired predetermined levels measured by comparators 60 and to provide operating power to the digital logic device 62.

It is to be appreciated that many variations of the circuitry illustrated in FIGS. 5a, 5b, 6 and 7 may be apparent to those of skill in the art. For example, it should be appreciated from the foregoing, that FIGS. 5a and 5b are equivalent alternatives. Therefore, whereas each of FIGS. 6 and 7 mimic the structure of FIG. 5b, it should be appreciated that either of FIGS. 6 and 7 may be implemented using the alternative structure of FIG. 5a. It is further to be appreciated that the digital logic device 62 may be provided with circuitry equivalent to any number of comparators, and not necessarily four as illustrated in FIG. 6 or eight as illustrated in FIG. 7. Implementations such as those shown in FIGS. 6 and 7 may be advantageous in that the digital logic device 62 may be very inexpensive and also offer flexibility in design options.

According to one aspect of the invention, the X-ray detector sub-system may be calibrated by detecting X-rays transmitted directly by the X-ray source, without an object to be inspected present in the inspection region. This is known as an "air" measurement, and, for example, for a dual energy system, respective H and LO air values may be obtained from these measurements. By normalizing the X-ray data obtained from the processor block against the respective HI and LO air values, HI and LO attenuation values may be obtained, corresponding respectively to the higher energy and lower energy portions of the X-ray spectrum. Accordingly, these HI and LO attenuation values may be used to calibrate a single X-ray detector, such as a Lunar detector, for dual energy detection.

Preferably, the process of determining the values needed to calibrate all of the detectors will be automated using calibration software running on processor 34 or other convenient computer data processor that is part of or connected to the inspection system.

In addition, various scintillator crystals, photodetectors and amplifier circuits in different channels of an X-ray detector subsystem may combine to produce some variation in electronic response to identical X-ray interaction events. Therefore, in order to compensate for these variations, a calibration procedure may be implemented. For example, the calibration may include exposing the detector system to stepped increases in X-ray energy potential, measuring the response for each step, and adjusting each channel (e.g., the resistor values or the offset signals from blocks 70 and 72) to produce uniform results. According to another example, a single adjustable resistor may be placed at the top of a resistor chain, so as to effectively reduce the monitored pulse voltages at the stages in the chain below it.

Alternatively, calibration can be accomplished by software adjustment to the multi-level counts observed from each detector. For example, histograms from nearby detectors could be equalized by numerical scaling during a training period or measurement and the same scaling could be applied during use of the system to inspect items of baggage, packages, cargo and the like. In another example, a combination of the above methods may be used to perform calibration.

According to another embodiment, the X-ray detector cells may be arranged in parallel, adjacent, linear diode arrays. These linear diode arrays together comprise a "multi-slice" detector. According to one example, the arrays may be arranged such that no detectors fall outside an umbra generated by the X-ray illuminating source. Such a multi-slice configuration may be useful in reducing the count rate required for polling the detector crystals. For example, using numerous smaller detectors in place of a larger detector results in a lower count rate in proportion to the fraction of the original area being monitored by each of the smaller detectors. Each of the smaller detectors is statistically less likely to have an x-ray interaction than a single larger detector. Smaller detectors also may have lower capacitance and may be more readily adapted for use with high speed electronics. The lower count rates permit use of more common scintillator material, such as CsI(Tl), since electrical pulses may not overlap as interactions in an individual detector occur less frequently. Another advantage of multi-slice detectors is the potential to increase the overall spatial resolution of the system.

According to one embodiment, the sampling rate, or the rate at which a detector crystal may be "polled," is determined, in part, by the overall capacitance of the detector material. The more material, the greater the capacitance, the slower the polling rate. Detectors that are capable of responding within a time period sufficiently small to capture a single X-ray photon event may, thus, be very small. The multi-slice configuration described above has the added advantage of increasing the overall image resolution of the system under discussion. By arranging linear diode arrays (LDA's) adjacent to each other in order to compensate for the spatial resolution differences, the resulting system may require fewer counting cycles per LDA and therefore, more detectors can be used per LDA in order to maximize image resolution orthogonal to the belt direction of an LDA system. In addition, pixel values in detector cells that are adjacent to each other, but lie on separate LDA's may be combined using standard image analysis and signal processing techniques in order to more accurately determine the appropriate pixel value at each coordinate space.

In the multi-slice configuration and using a conveyor speed appropriate for objects lying flat on the conveyor, point-like objects sufficiently distant from the X-ray source (i.e., closer to the detectors) may be imaged by one detector cell on an LDA and subsequently imaged by another detector cell lying in a different LDA. Thus, objects closer to the arrays may be more subject to imaging artifacts than objects far from the array. This aliasing artifact may be ameliorated by computationally blurring the image. A height detector may be used in order to determine whether or not blurring or other anti-aliasing techniques are to be used during image generation and analysis. The height data can be combined with the image data to make local adjustments to parameters used by the blurring or other anti-aliasing techniques. Alternatively, conveyor speed may be modulated in accordance with upstream height detector data to reduce height-dependent artifacts in the image. Resolution improvement may rely on parameters such as the physical arrangement of the detectors, measurement of bag height, conveyor speed, sampling time and the size of the focal spot as inputs to a deblurring, anti-aliasing or other image processing algorithm. For example, choice of a microfocus x-ray source may be useful for obtaining high resolution images with the multi-slice implementation.

Thus, according to some embodiments, the system may include means to reduce count rate by reducing the detector size or multiple-slice configuration, means to improve the multiple slice image by combining information from sequential attenuations from detectors monitoring the same belt position, and/or means to improve the multiple slice image by combining information from subsequent attenuations from detectors monitoring the same belt position with attenuations computed at various sampling intervals. Additionally, the multiple slice image may be improved by combining information from subsequent attenuations from detectors monitoring the same belt position and making use of height sensor information for deciding on how the information is combined.

Figure 8A:
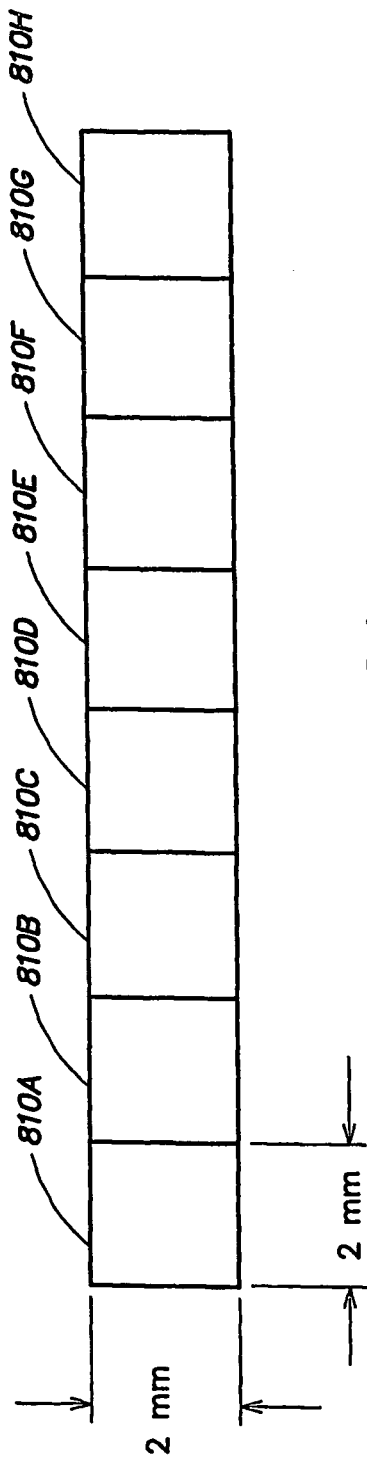
FIG. 8A is a sketch of linear arrays of detectors as in the prior art.
Figure 8B:
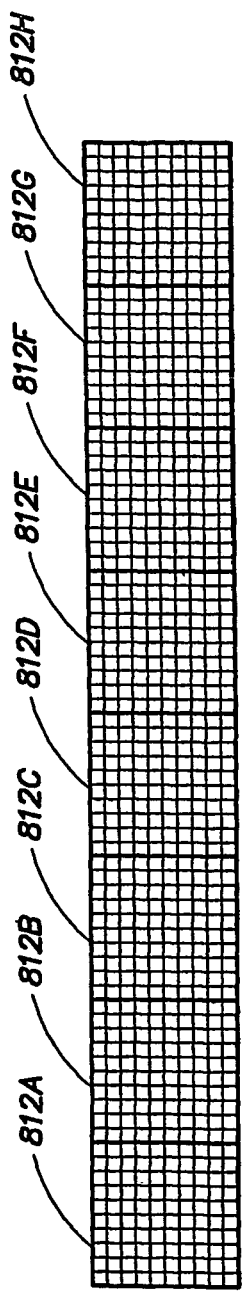
FIG. 8B is a sketch of a linear array of detectors.

FIG. 8A pictures a linear array of detector cells 810A, 810B . . . 810H. As described above, each cell has traditionally been approximately two millimeters square. FIG. 8B illustrates a preferred embodiment of a linear detector array. As described above, it is desirable for each of the detectors to be able to resolve individual interactions with a photon by outputting a pulse for each photon. To resolve individual interactions, each detector can be made sufficiently small that there is a small probability of two photons striking the detector so close in time that the pulses produced in response to each photon are smeared together. In a preferred embodiment, each detector will be less then one millimeter square. More preferably, each detector will be even smaller. Detectors sized to be 0.5 millimeters square or less are more preferred. In the presently contemplated embodiment, the detectors are 0.2 millimeters square. Each detector need not be as square shown in FIG. 8B. Any shape of roughly equivalent area is suitable.

Detectors as described above can produce data suitable for use with conventional image processing systems. For example, relative radiation levels can be measured by counting pulses from each detector in some interval of time. Counts of pulses can be used to compute attenuation by the item or scattering from the item, depending on the source/detector configuration. The data from the detectors might be used to create an image of the item being inspected and present that image to a human operator. Alternatively, automated detection algorithms might be used to determine whether an item contains contraband, such as explosives. Alternatively, automated object recognition might be used in combination with presenting an image to a human operator. In this scenario, automated object recognition is used to highlight suspicious objects in the item when the image is presented to a human operator. Having multiple small detectors in the same area as was occupied by a larger detector element in the prior art presents several possibilities for data processing.

One possibility is that the outputs of the smaller detectors might be processed separately. The data processing would therefore be performed at a much higher resolution. A second possibility is that the outputs of individual smaller detectors can be aggregated to produce values consistent with detector outputs that might occur if the detectors were of the same size as in the prior art. FIG. 8B shows that individual detector elements are grouped into groups such as 812A, 812B, 812C . . . 812H. In any given interval of time, the combined counts of all of the smaller detectors in these groupings would be taken as the value for the entire group.

Possibly, the resolution of the images might be set adaptively. It was described above that height measurements on items moving through an inspection system might be used as part of a process to avoid aliasing or imaging artifacts. FIG. 8C shows an item 850 moving transverse to the long dimension of the array of detectors shown in FIG. 8B. At successive intervals in time, radiation passing through a portion of item 850 will interact with a portion of the detector array. The cross section shown in FIG. 8C, will interact with just one of the groups 812A . . . 812H. The group corresponding the cross section shown is indicated as 812.

In FIG. 8C, the portion of item 850 being imaged on detector 812 is identified as $S_1$. FIG. 8D shows the same item 850 when the next sample is taken by the detector group 812. Between samples, the item 850 has moved a distance $D_1$. FIG. 8E shows the same item 850 at the subsequent sample. Item 850 has moved a distance $D_1$. In this position, portion $S_2$ is being imaged by detector group 812.

Object 852 is contained within portion $S_2$ of item 850. FIG. 8C shows portion $S_1$ being imaged and object 852 initially out of the path of radiation traveling from source 854 to detector 812. Therefore, the sample acquired from detector group 812 at the time depicted in FIG. 8C does not contain an indication of object 852. Processing of the acquired data would indicate that object 852 is not within portion $S_1$ of object 850.

FIG. 8D shows the same item 850 after it has moved along the conveyor a distance $D_1$. Portion $S_2$ of object 850 is in the path between the source and detector. In this position, object 852 has moved into the path between radiation source 854 and detector group 812. A "shadow" 862 of object 852 appears on detector 812. The shadow represents the areas where the radiation impinging on the detector has passed through the object. A sample taken in this configuration indicates that object 852 is within portion $S_2$ of item 850.

FIG. 8E shows the same item 850 after it has moved along the conveyor by a further distance $D_1$ and portion $S_3$ is above the source. At this time, object 852 has moved out of the path of the radiation between source 854 and detector 812. In this condition, object 852 does not impact the radiation received at detector 812 and does not appear in the image of item 850. A sample taken in the configuration of FIG. 8E indicates that object 852 is not within portion $S_3$ of item 850. For an item 850 as shown, the data collected from detectors 812 and 813 can be easily used to build an image and identify the position of object 852 within item 850.

Figure 8H:
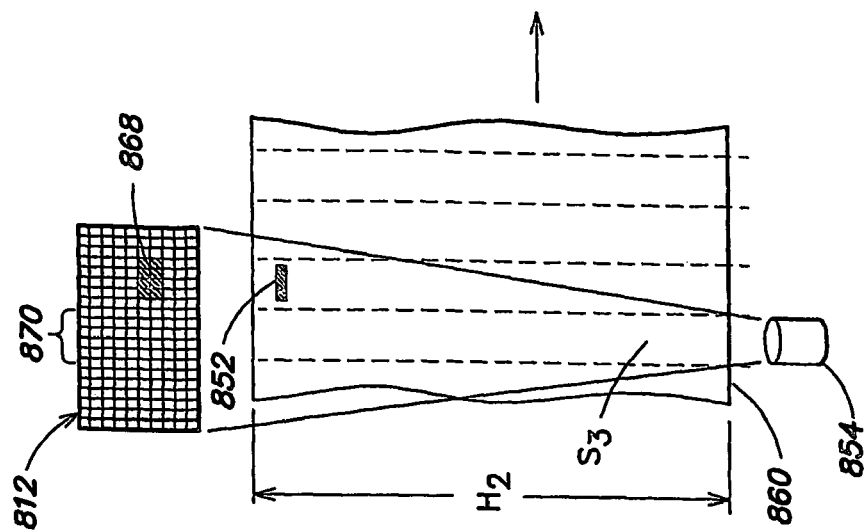
Figure 8G:
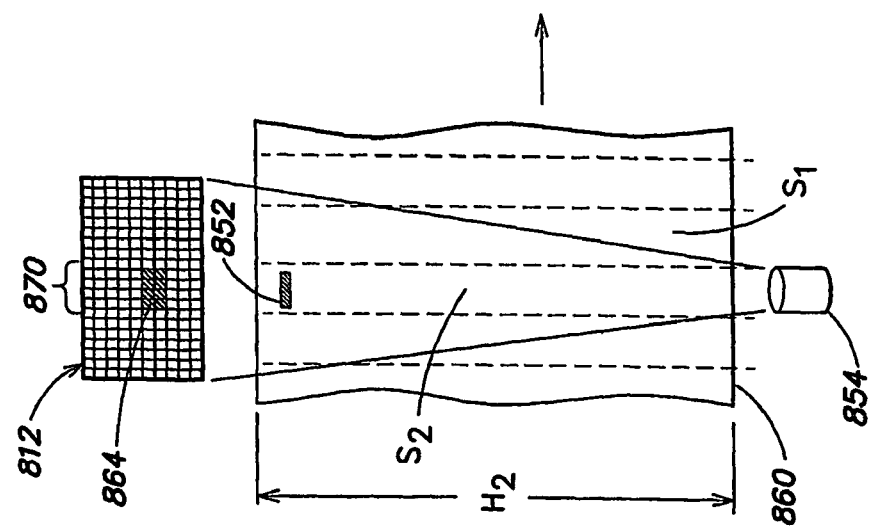
Figure 8F:
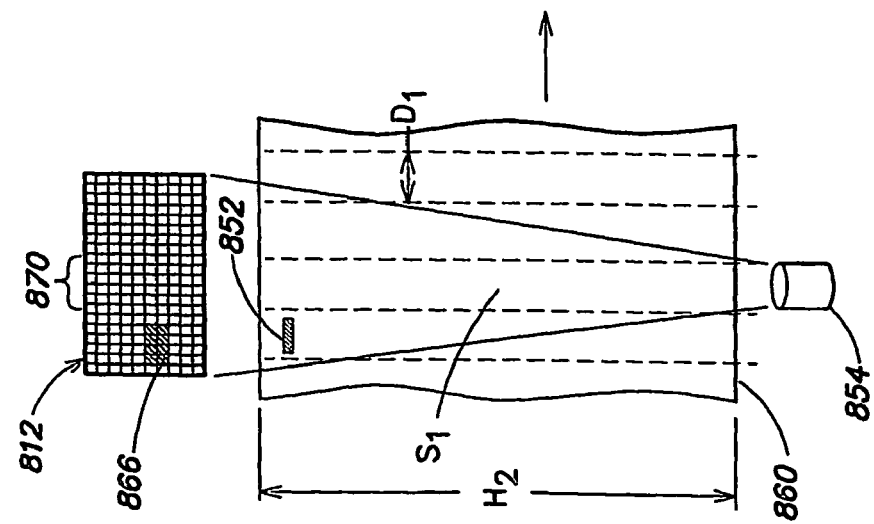

FIGS. 8F, 8G and 8H show the same object 852 positioned in an item of 860. Item 860 has a height $H_2$ that is much taller than $H_1$. As a result, object 852 is positioned much closer to detector group 812. The series of FIGS. 8F, 8G and 8H shows imaging artifacts that can occur if an attempt is made to image an item with too great a spatial resolution.

FIG. 8G shows the item 860 positioned with portion $S_2$ above source 854. Object 852 is in portion $S_2$ and the shadow 864 of object 852 falls on detector 812. Data collected in this position will indicate that object 852 is within portion $S_2$.

However, a shadow 866 of a portion of object 852 also falls on detector 812 when item 860 is positioned as shown in FIG. 8F. In the configuration shown in FIG. 8F, portion $S_1$ is about the source 854. A similar condition exists with respect to the configuration of FIG. 8H. In that configuration, even though portion $S_3$ is above source 854, object 852 makes a shadow 868 on detector 812. Thus, data collected from the series of samples in FIGS. 8F, 8G and 8H indicate that object 852 is in all three portions: $S_1$, $S_2$ and $S_3$.

The sequence show in FIGS. 8F, 8G and 8H is an example of spatial aliasing. The spread of the beam from source 854 combined with the height of the object above the source creates this condition. The aliasing might be avoided by decreasing the spatial resolution of the imaging system when tall items—that create the possibility of objects being far from the source—are being imaged.

One way that the spatial resolution of the inspection system might be selectively decreased is shown in FIGS. 8I and 8J. In these figures, the conveyor moves item 860 a distance $D_2$ between samples. As shown in these pictures, movement by an amount $D_2$ is sufficient to ensure that object 852 makes a shadow in only one sample taken with detector group 812. A disadvantage of this approach is that objects, such as 880, close to source 854 might not be imaged at all.

An alternative approach is suggested by FIGS. 8F, 8G and 8H. If just a portion of the detectors in detector group 812 are used to gather data for tall objects, the chances of aliasing are significantly reduced. If only the detectors within region 870 are used to form an image, the shadow 864 will be recorded. However, the undesirable shadows 866 and 868 will not be recorded.

In one embodiment, the height of the item being inspected is measured and the number of detectors in detector group 812 used for forming an image is selected. The number of detectors in selected in inverse proportion to the height.

The area of detector group 812 could be made smaller so that it matched the size of region 870. The drawback of this approach, however, is that making detector group 812 smaller reduces the spatial resolution even for shorter items being inspected. FIG. 8D shows that the spread of radiation from source 854 creates magnification in the image that is most pronounced for items close to the source. Thus, shadow 862 is larger than shadow 864 even though these shadows both represent object 852. If only the detectors in region 870 of detector group 812 are used to form an image, information about the exact position and size of object 852 is lost. The data gathered will still indicate that object 852 is present within portion $S_2$. However, the data would appear indistinguishable from data collected from a smaller object that cast a shadow fully across region 870 or an object positioned further to the left or right within portion $S_2$.

On the other hand, if the full output of detector group 812 is used to process the image data depicted in FIG. 8D, the magnification yields a higher resolution image. Having detector groups made of numerous small detectors facilitates changing the area of each detector. By selecting the number of detectors in the detector group used to form an image based on the position of the object relative to the source, higher resolution images can be made, when possible, and aliasing can be avoided. Measuring the height of the item under inspection is one simple way to select the number of detectors in the detector group used to form an image.

FIG. 8K shows an alternative condition that might occur because of multiple small detector elements. When the detector elements are very small and close together, a single photon and its progeny might interact with multiple detectors. FIG. 8K shows that detectors 820A, 820B, 820C and 820D are producing an output because of a single incident photon. If each detector producing an output pulse where counted, the incident photon would be counted four times, once for each detector 820A, 820B, 820C and 820D. Accordingly, it might be desirable to create an inspection system with multiple small detector elements that includes circuitry to provide local aggregation of coincident events. In the example of FIG. 8K, such circuitry would identify pulses produced by detectors 820A, 820B, 820C and 820D as resulting from the same incident photon. Therefore only one photon would be counted even though four detectors produced pulses at their outputs.

Various implementations of such a circuit are possible. The simplest is to sum the output signals of all detectors in a given "super cell" area before counting pulses. Optionally, circuitry to affirmatively suppress the output of any detector in the super cell area that is not responding might be included to reduce the noise added upon local aggregation of coincident events. In scenarios where the total energy of the incident radiation is not measured, an alternative approach might be to suppress the output of one detector if an adjacent detector produced an output within some relatively small period of time. Alternatively, the circuitry to record events from the individual detectors in a localized region might be time multiplexed, which could inherently suppress the outputs of some detectors while the output so of others are being recorded.

Alternatively, the outputs of all the detectors might be captured and subsequent processing—either in hardware or software—could provide for a local aggregation of coincident events.

Figure 9A:
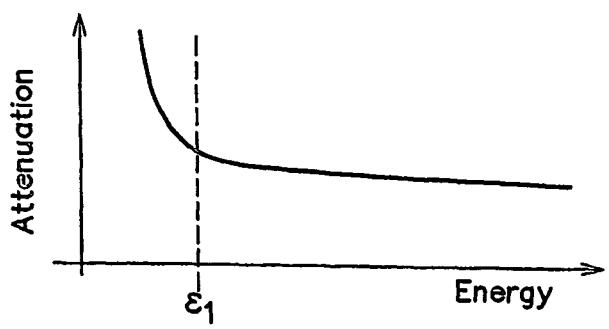
FIGS. 9A 9B are graphs illustrating attenuation profiles useful in understanding an application of the detector circuits described above.

FIGS. 9A, 9B, 9C and 9D show further advantages that can be achieved. In particular, detectors that produce output pulses in response to photons allow the amplitude of those pulses to be used to gather more information about objects within the item being inspected. FIG. 9A indicates attenuation versus x-ray energy for a material of low atomic number. It is known that materials of different atomic number have different attenuation versus energy profiles. This phenomenon has served as the basis for prior art dual energy inspection systems. Attenuation at two energy levels were measured for the same object. By computing the ratio between the attenuation at these energy levels, an indication of the effective atomic number of the object being inspected was produced.

Figure 9B:
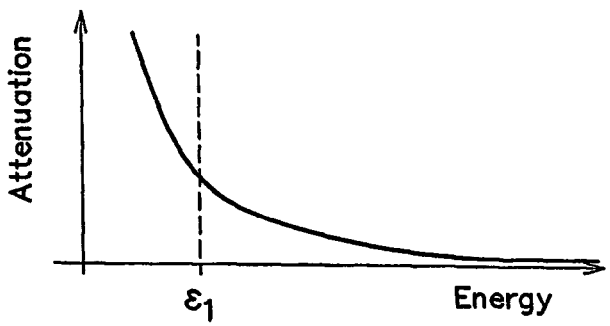

FIG. 9B indicates the attenuation versus x-ray energy for a much thinner amount of material of moderate atomic number, such as iron. For higher energy photons, there is very little attenuation.

Prior art inspection systems indicated material that responded differently to x-rays of different energies. However, such inspection systems generally required different types of detectors for each energy at which a measurement is made.

Figure 9C:
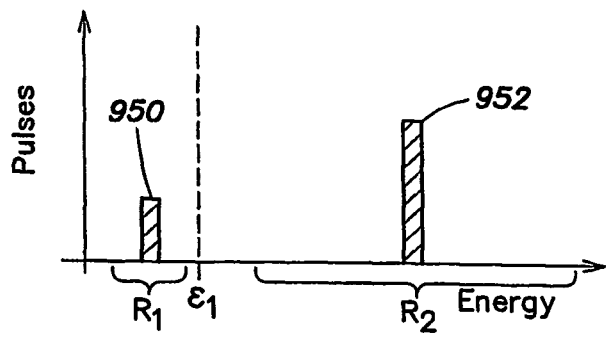
FIGS. 9C and 9D are graphs illustrating counts of useful in understanding a method of estimating effective atomic number.

FIG. 9C shows how the type of detectors described above can be used to make dual energy measurements. As described above, each detector produces an output pulse in response to a photon. The magnitude of the pulse indicates the energy of the photon. By establishing thresholds before counting pulses from a detector, the number of pulses having a magnitude within multiple ranges can be counted. These ranges can be correlated to an energy range.

Figure 9D:
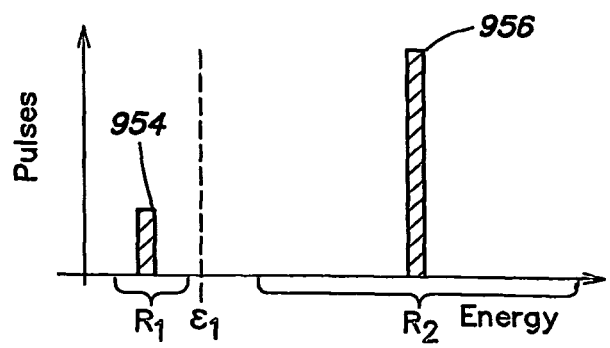

For example, FIG. 9C shows an energy range $R_1$ and $R_2$. Bars 950 and 952 indicate the number of pulses counted over some interval falling into each range. FIG. 9C shows counts consistent with an attenuation versus energy profile of FIG. 9A. FIG. 9D shows similar bars 954 and 956 for a material having an attenuation versus energy profile of FIG. 9B. As can be seen, the relative number of counts in range $R_1$ and $R_2$ allows an inspection system to distinguish between a material as indicated by the curve in FIG. 9A and the one indicated in FIG. 9B. More generally, a comparison of the number of counts in different ranges allows an indication of the atomic number of a material to be determined.

Figure 9E:
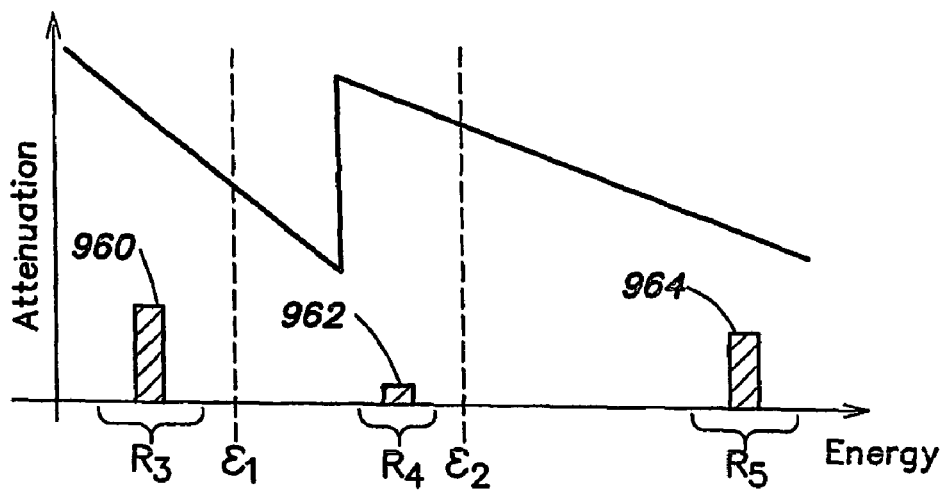
FIGS. 9E and 9F are graphs illustrating attenuation profiles useful in understanding an application of the detector circuits described above.
Figure 9F:
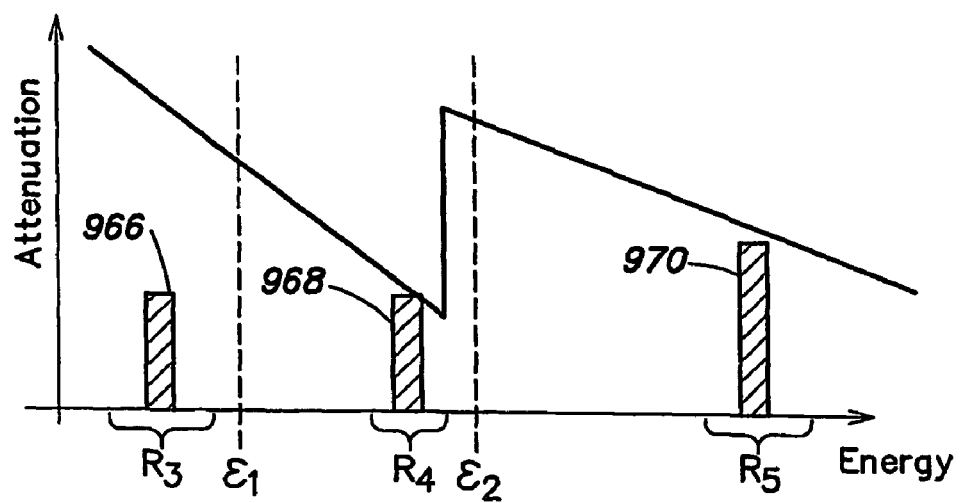

FIGS. 9E and 9F illustrate a further advantage that can be obtained with detectors as described above. The data out of one set of detectors can be processed to identify counts in multiple ranges, thereby allowing more accurate identification of materials. FIGS. 9E and 9F show the attenuation versus energy profiles of samples of materials of higher atomic number. Even though these materials have similar attenuations at some energies, they have overall different profiles.

FIG. 9E shows three ranges $R_3$, $R_4$ and $R_5$. Superimposed on the attenuation versus energy profile is a series of bars 960, 962 and 964. FIG. 9F also shows the attenuation versus energy profile of a different material of high atomic number. Bars 966, 968 and 970 show the counts in the same energy ranges. Comparison of the relative heights of the bars in these ranges allows a distinction between the materials depicted in FIGS. 9E and 9F. More generally, comparison of the relative counts in three or more ranges allows even more accurate identification of materials by their effective atomic number.

A further advantage is that, because the energy ranges are created by processing data from a detector—rather than from different types of detectors—the specific energy bands can be readily programmed based to enable an inspection system to search for specific materials. For example, the profiles shown in FIGS. 9E and 9F both have approximately equal attenuations around an energy of $\epsilon_2$. Making measurements in a narrow energy range centered around $\epsilon_2$ would not yield good results in discriminating between materials as depicted in FIGS. 9E and 9F. If one of the materials represented in FIGS. 9E and 9F is contraband and the other is not, attempting to identify materials based on measurements in an energy range centered around $\epsilon_2$ would not yield optimal results.

On the other hand, the profiles depicted in FIGS. 9E and 9F have "notches" or other features that are different for different types of materials. Making measurements in multiple energy bands, with some of the bands narrowly centered around a readily recognizable characteristic of a materials of interest, would lead to more accurate identification of materials.

An inspection system using detectors as described above could exploit this property to perform material specific scans by choosing energy bands that would highlight characteristic features of the material. For example, scans could be tailored for certain types of explosives or other contraband of concern. Even more thorough inspections could be made by making measurements at even more energies. In the limit, data processing might be used to create measurements in so many energy bands that the entire attenuation versus energy profile of a material is created.

In a preferred embodiment the contraband detection system will process the output of detectors that allow determination of attenuation at multiple energy threshold ranges. Because the behavior of high atomic number materials allows better discrimination of atomic make-up, use of additional threshold ranges is particularly advantageous for discriminating such materials. Of these multiple thresholds, preferably two or more will be at a relatively high energy level where greatest discrimination of materials of high atomic number can be obtained. In the preferred embodiment at least two energy level thresholds will be above 20 keV and more preferably at least two energy levels will be above 40 keV.

Also, it should be appreciated that the figures show relatively sharp lines denoting boundaries of energy ranges. It should be appreciated that practical components will not respond with such precision to allow such sharp discrimination based on the energy of a photon and that an energy "bin" or "range" need not correspond to sharp transition regions as shown.

Using multiple energy thresholds also aids in the identification of and compensation for gain shifts in the detectors. As the gain of a detector shifts, the magnitude of pulses produced by the detector will shift. A gain shift, therefore, has the unwanted impact of counting some pulses, that prior to the gain shift would have been recorded having an energy below $\epsilon_1$, in a range associated with an energy above $\epsilon_1$. By examining the relative counts in multiple ranges, the shifts might be identified and compensated in hardware or software.

Also, FIGS. 9E and 9F are identified as attenuation versus energy profiles. The detectors actually measure radiation intensity. Attenuation is generally derived by comparing relative intensities of detected radiation with and without an item in the system. However, the detectors are not limited to use in application where attenuation is measured. For example, the detectors might be used in a system in which scattered radiation is detected. The energy of scattered photons often indicates the type of material from which the radiation was scattered. Therefore, having one type of detector that can measure the intensity over multiple ranges would also be desirable for identifying materials from scattered radiation.

Having thus described various embodiments and aspects thereof modifications and alterations may be apparent to those of skill in the art.

For example the type of radiation source used is not critical to the invention. An x-ray source could be used. However, a gamma ray source might also be used. Herein, the term "photon" is used to refer generally to electromagnetic radiation.

The specific beam configuration is also not critical. For example, a beam of radiation with a fan pattern might be used to simultaneously illuminate multiple detectors over a relatively wide area. Alternatively, a pencil beam might be used such that detectors in a far smaller area are simultaneously illuminated. Alternatively, the x-ray source might be used with or without a collimator as a way to control the number of detectors simultaneously illuminated.

Further, a single stationery source might be used to provide the radiation. Alternatively, a single moving source might be used to provide radiation. For example, where CT images are desired, a source might rotate around the item being inspected. Further, computed tomographic images of an item might be created from the source that does not rotate 360° around the item. The source might rotate only 180°. Or, similar images might be created with multiple stationary sources that irradiate the item from different directions.

Also, it is described that items move through the inspection system on a conveyor belt. However, any convenient means to provide relative motion between the source, in the detector and detector pair and the item being inspected could be used. The source or the item might move. For example, the item might be contained in a truck moving past a fixed source and detector. Alternatively, the source or detector might be mounted on a boom that moves relative to the item. Such a conveyance system is well suited for inspecting cargo containers.

In addition, one dimensional arrays of detectors are shown to be in a straight line. However, one-dimensional arrays need not be in a straight line. Detectors arranged in an L-shape or other configurations may be termed one dimensional arrays.

Further, specific calibration circuitry is described as an example. It should be appreciated that the amount and type of correction will depend on the properties of the detectors used. For detectors in which the variability from detector to detector appears as a linear error, any circuit that provides gain and offset correction might be used. For some detectors, the error properties will be such that only gain or only offset will provide adequate correction. For detectors that exhibit nonlinear error characteristics, higher order correction factors might be employed in addition to gain and offset correction. Alternatively, for nonlinear errors, a calibration table or similar technique might be used.

It should also be appreciated that the preferred embodiment describes correction factors applied using a hardware circuit. Comparable corrections can be applied with software processing to data collected from uncalibrated detectors.

Further, a system in which the height of an object is detected and used in the processing of image data. More generally, any means for estimating the distance between the source and the item might be used. For example, the distance could be measured with a hardware device, such as: an electronic eye that detects the position of the item when the item breaks a light path between a light source and a detector; a laser range finder, an acoustic range finder, etc. Alternatively, distance can be estimated by processing an image of the item and observing the position of the item as reflected in the image.

In addition, the detectors are described as being used in connection with a contraband detections system. The outputs of the detectors might be used to display an image of an item under inspections so that objects within the image might be identified. The image might be presented with different colors or gray-scales showing density or atomic number of objects within the item. Or, the outputs of the detectors representing attenuations in different energy ranges might be used in a computation called a basis function decomposition. Such a computation is useful in making an image that is relatively insensitive to beam hardening effects.

Further, it is not necessary that the outputs of the detector be used solely to create an image. The outputs might be used in decision making, such as to identify contraband or threat material inside an item. Or, the outputs of the detectors might be used to identify desirable objects. For example, the system might make a decision as to whether a sample of ore contains base metal or valuable minerals.

Such modifications are intended to be covered by this disclosure which is for the purpose of illustration only and not intended to be limiting.

The invention claimed is:

1. A system for inspecting an item, comprising:
   a) a radiation source emitting a plurality of photons;
   b) a plurality of radiation detectors positioned to receive radiation from the radiation source after the radiation interacts with the item and to produce a pulse in response to a photon, each of the radiation detectors having a scintillating member and a light detector with a solid state element positioned to receive light from the scintillating member;
   c) a conveyance system for providing relative motion between the item and the path of radiation from the radiation source;
   d) a plurality of channels, each channel having:
      i) an input connected to an output of a respective radiation detector, and
      ii) an output representative of a number of pulses produced by the respective radiation detector during an interval of time; and
   e) a data processor receiving as inputs the outputs of the plurality of channels, the data processor processing the inputs to determine characteristics of objects within the item.

2. The system for inspecting an item of claim 1, wherein the output of each of the channels comprises a plurality of values, each value representing the number of pulses produced by the respective radiation detector with an amplitude in a predetermined range.

3. The system for inspecting an item of claim 1, wherein the solid state element comprises a photodiode.

4. The system for inspecting an item of claim 1, wherein each radiation detector produces a pulse in response to a photon, the pulse having a rise and decay time of less than 40 nanoseconds.

5. The system for inspecting an item of claim 1, wherein the radiation source is an x-ray source.

6. The system for inspecting an item of claim 1, wherein the radiation source moves at least partially around the item and the data processor performs a computed tomographic reconstruction of the item.

7. The system for inspecting an item of claim 1, wherein the conveyance system comprises a conveyor belt moving relative to the source.

8. The system for inspecting an item of claim 1, wherein the scintillating member comprises a crystal with a chemical composition including at least one rare earth element.

9. The system for inspecting an item of claim 7, wherein the plurality of radiation detectors comprises a two dimensional array, the array being disposed along a direction of travel of the conveyor belt.

10. The system for inspecting an item of claim 9, wherein the data processor produces a representation of one portion of an item by combining outputs of channels coupled to radiation detectors in different subgroups of the two-dimensional array at different times.

11. The system for inspecting an item of claim 9, wherein each detector has an area less than 0.2 mm$^2$.

12. The system for inspecting an item of claim 1, wherein each radiation detector is sized to receive radiation from the radiation source passing through an area of the item having a dimension of no more than 2 mm.

13. The system for inspecting an item of claim 1, wherein each of the channels comprises at least one level sensitive circuit having an input coupled to the output of a radiation detector, each level sensitive circuit producing an output in response to an input exceeding a predetermined level.

14. The system for inspecting an item of claim 13, wherein the output of each of the at least one level sensitive circuits is used in the image processor as an indication of the energy level of a photon interacting with the radiation detector.

15. The system for inspecting an item of claim 14, further comprising counting circuitry coupled to the outputs of each of the at least one level sensitive circuitry, the counting circuits producing counts of the number of photons above at least one threshold energy interacting with each of the radiation detectors.

16. The system for inspecting an item of claim 14, wherein each channel additionally comprises a calibration circuit coupled to each of the at least one level sensitive circuits to change the predetermined level for each of the level sensitive circuits.

17. The system for inspecting an item of claim 14, wherein:
   a) each of the channels comprises at least two level sensitive circuits and the output of the channel comprises at least two values, each value indicative of the number of pulses exceeding the a predetermined level of each of the at least two level sensitive circuits in an interval of time; and
   b) the data processor computes a representation of the effective atomic number of a portion of an item from the relative values of the at least two values output from a group of channels, the group containing at least one channel.

18. The system for inspecting an item of claim 13, further comprising calibration circuitry coupled to the level sensitive circuits in each of a plurality of channels, the calibration circuitry adjusting the predetermined levels of the level sensitive circuits in each of said plurality of channels to give a more nearly equal to photons of similar energy levels response from level sensitive circuits coupled to adjacent radiation detectors.

19. The system for inspecting an item of claim 18, wherein the calibration circuitry adjusts the predetermined level by providing an offset to a predetermined value, wherein an offset is applied for each channel.

20. The system for inspecting an item of claim 18, wherein the calibration circuitry adjusts the predetermined level by providing a gain to a predetermined value, wherein a gain is applied for each channel.

21. The system for inspecting an item of claim 1, further comprising a plurality of pulse amplitude measuring circuits, each pulse amplitude measuring circuit having an input coupled to the output of a radiation detector and an output indicating the amplitude of a pulse produced by the radiation detector.

22. The system for inspecting an item of claim 21, wherein the plurality of pulse amplitude measuring circuits comprises at least one analog to digital converter.

23. The system for inspecting an item of claim 22, wherein the plurality of pulse amplitude measuring circuits comprises at least one integration circuit configured to integrate energy in a pulse produced by at least one radiation detector and the analog to digital converter is coupled to the radiation detector through the integration circuit.

24. The system for inspecting an item of claim 22, wherein the plurality of pulse amplitude measuring circuits comprises at least one sampling circuit and the analog to digital converter is coupled to the radiation detector through the sampling circuit.

25. The system for inspecting an item of claim 24, wherein the sampling circuit has a sampling interval that is short in comparison to the duration of a pulse produced by the detector.

26. The system for inspecting an item of claim 21, wherein the data processor is coupled to the pulse amplitude measuring circuits and the data processor counts pulses falling within predetermined ranges of amplitudes and different predetermined ranges are selected for different ones of the plurality of detectors using data gathered during a calibration routine.

27. The system for inspecting an item of claim 1, wherein each of the channels comprises circuitry for aggregating coincident outputs of adjacent detectors.

28. The system for inspecting an item of claim 1, wherein the data processor makes a decision based on the characteristics of an object within the item.

29. The system for inspecting an item of claim 1, wherein the decision comprises outputting an indication of threat material within the item.

30. The system for inspecting an item of claim 1, further comprising a means for estimating the distance between the radiation source and the item.

31. The system for inspecting an item of claim 30, wherein the outputs of a plurality of detectors are aggregated prior to processing by the data processor selectively in response to the output of the height detector.

32. The system for inspecting an item of claim 31, wherein the number of detectors for which the outputs are aggregated is greater when the item has a height exceeding a threshold than when the item is below the threshold.

33. The system for inspecting an item of claim 31, further comprising a display displaying an image of the item derived from the outputs of each of the channels and the display has a greater resolution when the item has a height below the threshold.

34. A system for inspecting an item, comprising:
  a) a radiation source emitting a plurality of photons;
  b) a plurality of means for producing identifiable pulses, each pulse being produced in response to an individual interaction between a photon from the radiation source and a scintillation detector after the radiation has interacted with a portion of the item;
  c) means to position the item in the path of radiation from the radiation source;
  d) a plurality of channels, each channel comprising means for making a plurality of counts of pulses produced by one of the plurality of means for producing, each of the counts representing a number of pulses with an amplitude in a predetermined range; and
  e) means for analyzing the counts of pulses to form a representation of the item.

35. The system for inspecting an item of claim 34, wherein each scintillation detector has an active area facing the radiation source of less than 1 square mm.

36. The system for inspecting an item of claim 34, wherein each scintillation detector has an active area facing the radiation source of less than 0.2 $mm^2$.

37. The system for inspecting an item of claim 34, additionally comprising:
  means for using the representation of the item for identifying contraband inside the item.

38. The system for inspecting an item of claim 34, wherein the means for making a plurality of counts comprises means for counting pulses representative of photons in two energy bands.

39. The system for inspecting an item of claim 38, wherein the radiation source generates radiation at energies below 150 KeV.

40. The system for inspecting an item of claim 34, wherein the means for analyzing comprises means for combining counts of pulses produced by different ones of the plurality of means for producing identifiable pulses made at different times.

41. The system for inspecting an item of claim 40, additionally comprising a measurement device adopted to estimate a distance between the radiation source and the item, and wherein the means for combining is responsive to the distance.

42. The system for inspecting an item of claim 34, comprising means for reducing the rate at which pulses are generated by the means for producing identifiable pulses.

43. The system for inspecting an item of claim 42, wherein the means for reducing the rate at which pulses are generated comprises a plurality of arrays of small detectors.

44. A method of operating a system for inspecting an item comprising a plurality of detectors that each produces a pulse in response to a photon incident on the detector, the method comprising:
  a) calibrating the plurality of detectors to correlate the level of the pulse produced by each detector with an energy levels photons incident on the detector;
  b) counting pulses with levels representative of a least three energy levels produced by the plurality of detectors;
  c) combining the counts of the pulses into a representation of the item; and
  d) analyzing the representation of the item to determine properties of objects within the item based in part on the relative number of counts of each energy level.

45. The method of claim 44, wherein the pulses have a magnitude representative of the energy of the photon interacting with the detector and combining the counted pulses into a representation of the item includes an indication of the atomic number of material within the item derived from relative counts of pulses with different magnitudes.

46. The method of claim 45, wherein calibrating the plurality of detectors comprises:
  radiating the plurality of detectors without an item present and collecting calibration data; and the method additional comprises scaling the magnitude of the pulses from each detector based on the calibration data prior to combining the counted pulses into a representation of the item.

47. The method of claim 44, additionally comprising moving the item relative to a detector array and combining counts of pulses generated by different detectors at different times representing photons passing through the same area of the item.

48. The method of claim 44, wherein the at least three energy levels comprises at least two energy bins above 20 keV.

49. The method of claim 48, wherein the at least three energy levels comprises at least two energy bins above 40 keV.

* * * * *